United States Patent
Wang et al.

(10) Patent No.: US 7,863,203 B2
(45) Date of Patent: Jan. 4, 2011

(54) MONOSILANE OR DISILANE DERIVATIVES AND METHOD FOR LOW TEMPERATURE DEPOSITION OF SILICON-CONTAINING FILMS USING THE SAME

(75) Inventors: Ziyun Wang, Bethel, CT (US); Chongying Xu, New Milford, CT (US); Thomas H. Baum, New Fairfield, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 12/019,557

(22) Filed: Jan. 24, 2008

(65) Prior Publication Data
US 2008/0160174 A1 Jul. 3, 2008

Related U.S. Application Data

(63) Continuation of application No. 10/683,501, filed on Oct. 10, 2003, now Pat. No. 7,579,496.

(51) Int. Cl.
*H01L 21/31* (2006.01)
*H01L 21/469* (2006.01)

(52) U.S. Cl. .............. 438/793; 438/789; 257/E21.478; 257/E21.493

(58) Field of Classification Search .............. 438/793, 438/789, 786; 427/255.28, 255.37, 255.394, 427/255.393; 257/E21.478, E21.487, E21.493, 257/E21.494
See application file for complete search history.

(56) References Cited

U.S. PATENT DOCUMENTS

| | | | |
|---|---|---|---|
| 5,204,141 A | 4/1993 | Roberts et al. | |
| 5,424,095 A | 6/1995 | Clark et al. | |
| 5,744,196 A | 4/1998 | Laxman et al. | |
| 5,939,333 A * | 8/1999 | Hurley et al. | 438/791 |
| 5,990,541 A * | 11/1999 | Saito et al. | 257/635 |
| 6,383,955 B1 | 5/2002 | Matsuki et al. | |
| 6,410,463 B1 | 6/2002 | Matsuki | |
| 7,064,083 B2 | 6/2006 | Dussarrat et al. | |
| 2003/0129826 A1 * | 7/2003 | Werkhoven et al. | 438/627 |
| 2004/0096582 A1 | 5/2004 | Wang et al. | |
| 2004/0121085 A1 * | 6/2004 | Wang et al. | 427/569 |

(Continued)

FOREIGN PATENT DOCUMENTS

EP 1 441 042 A1 7/2004

(Continued)

OTHER PUBLICATIONS

Wannagat U., et al "Si-N Compounds. LIII. Si-N2H4 compounds. 7. some new hydrazinosilanes", Monatshefte fuer Chemie(1965). 96(6), 1902-8.(Abstract ).*

(Continued)

*Primary Examiner*—Caridad M Everhart
(74) *Attorney, Agent, or Firm*—Steven J. Hultquist; Hultquist IP; Margaret Chappi

(57) ABSTRACT

This invention relates to silicon precursor compositions for forming silicon-containing films by low temperature (e.g., <550° C.) chemical vapor deposition processes for fabrication of ULSI devices and device structures. Such silicon precursor compositions comprise at least a silane or disilane derivative that is substituted with at least one alkylhydrazine functional groups and is free of halogen substitutes.

16 Claims, 4 Drawing Sheets

U.S. PATENT DOCUMENTS

| | | |
|---|---|---|
| 2004/0138489 A1 | 7/2004 | Wang et al. |
| 2004/0146644 A1 | 7/2004 | Xiao et al. |
| 2005/0037627 A1* | 2/2005 | Dussarrat et al. ............ 438/778 |
| 2005/0080285 A1 | 4/2005 | Wang et al. |
| 2005/0080286 A1 | 4/2005 | Wang et al. |
| 2009/0084288 A1 | 4/2009 | Wang et al. |

FOREIGN PATENT DOCUMENTS

| | | | | |
|---|---|---|---|---|
| FR | 2693204 | * | 1/1994 | ............... 528/20 |
| JP | 2000-080476 A | | 3/2000 | |

OTHER PUBLICATIONS

T. P. Smirnova et al "Composition and Structure of films deposited from silyl derivatives of assymetric dimthyl hydrazines" Inorg. Mat. vol. 39, No. 2 (2003), pp. 117-122.*

Wannagat "Uber die Hypergolitat von Silylhydrazinen" Monatschefte fuer Chemie (1966) vol. 97, No. 4, pp. 157-162.*

Sergeeva, et al., "Chem. Abstract 1960:127948; 'Synthesis of alkyl- and dialkylbis(1,1-dialkylhydrazino)silanes'", "Zhurnal Obshceii Khimii", 1960, pp. 694-695, vol. 30.

Chen, L.C., et al., "Crystalline silicon carbon nitride: A wide band gap semiconductor", "Appl. Phys. Letters.", May 11, 1998, pp. 2463-2465, vol. 72, No. 19.

Denk, Michael, et al., "Synthesis and Structure of a Stable Silylene", "J. Am. Chem. Soc.", Mar. 23, 1994, pp. 2691-2692, vol. 116, No. 6.

Gibson, George, et al., "The Reaction of Silicon Tetrachloride with N,N-Dimethylhydrazine and Hydrazine", "Inorg. Chem.", Aug. 1963, pp. 876-878, vol. 2, No. 4.

Lee, Gyun-Hwan, et al., "Bis[bis(trimethylsilyl)amino]silylene, an Unstable Divalent Silicon Compound", Jul. 9, 2003, pp. 8114-8115, vol. 125, No. 27.

Scherer, Otto, et al., "Ethylenimine and imidazolidinone derivatives of silicon", "Chem. Abstracts", 1965.

Sergeeva, Z.I., et al., "A new method of synthesis of organosilicon hydrazines (Chem. Abstracts 1963:27415)", "Zhurnal Obshchei Khimii", 1962, pp. 1987-1993, vol. 32.

Smirnova, T.P., et al., "Plasma-enhanced chemical vapor deposition of silicon carbonitride films from volatile silyl derivatives of . . . ", "Proceedings of the 3rd Symposium on Theoretical and Applied Plasma Chemistry, High Energy Chemistry", 2003, pp. 303-309, vol. 37, No. 5.

Smirnova, T.P., et al., "SiCN alloys obtained by remote plasma chemical vapour deposition from novel precursors", "Thin Solid Films", Apr. 1, 2003, pp. 144-151, vol. 429, No. 1-2.

Wannagat, Ulrich, et al., "Chem. Abstracts 1959:93473—abstract of 'Hydrazine-silicon compounds II Mixed alkyl-or aryl-substituted hydrazines'", "Z. anorg. u allgem. Chem.", 1959, pp. 341-348, vol. 299.

Wannagat, U., et al., "Chem Abstract 1966:104351; 'Si-N compounds. L-III. Si-N2H4 compounds. 7. Some new hyrdazinosilanes'", "Monatshefte fuer Chemie", 1965, pp. 1902-1908, vol. 96, No. 6.

West, Robert, et al., "Tetramesityldisilene, a Stable Compound Containing a Silicon-Silicon Double Bond", "Science", Dec. 18, 1981, pp. 1343-1344, vol. 214, No. 4527.

West, Robert, et al., "Stable silylenes: Synthesis, structure, reactions", "Pure & Appl. Chem.", 1996, pp. 785-788, vol. 68, No. 4.

West, Robert, et al., "Chemical Shift Tensors and NICS Calculations for Stable Silylenes", "J. Am. Chem. Soc.", Feb. 25, 1998, pp. 1639-1640, vol. 120, No. 7.

"Wikipedia Entry for the term 'Vapor Pressure'", "Found online at http://en.wikipedia.org/wiki/Vapor_pressure", Jul. 17, 2007.

Witte-Abel, Henning, et al., "Kondensationen von Silylhydrazinen und Estern zu Silylhydrazonen und Pyrazolnen", "J. Organometallic Chem.", Aug. 15, 1999, pp. 341-347, vol . 585, No. 2.

Sergeeva, et al., "Synthesis of 1,1-dialkyl-2-(trialkylsilyphydrazines (CAPLUS Abstract)", "Khim. i Prakt. Primenenie Kremneorg. Soedinenii", 1958, pp. 235-241, No. 1.

Voronkov, et al., "Izvestiya Vysshikh Uchebnykh Zavedenii (No English Abstract Available)", "Materialy Elektronnoi Tekhniki", 2002, pp. 57-60, vol. 4.

Mitzel, Morbert W., "Simple silylhydrazines as models for Si-N beta-donor interactions in SiNN units", "Chem. Eur. J.", 1998, pp. 692-698, vol. 4, No. 4.

Sergeeva, Z. I., et al., Caplus Abstract 1963:455161, 1963.

Sergeeva, Z. I., et al., Reaction of nonsymmetric dialkylhydrazines with alkylchloro-silanes (Caplus Abstract 1963:455161), Zhurnal Obshchei Khimii, 1963, pp. 1874-1878, vol. 33, No. 6.

(CAPLUS Abstract): Wannagat, U., et al., "Chem Abstract 1966:18737; 'Silicon-Nitrogen compounds. LXI. Silicon-hydrazine compounds. 11. Hypergolity of silyhydrazine", "Monatshefte fuer Chemie", 1966, pp. 1157-1162, vol. 97, No. 4.

Unpublished U.S. Appl. No. 12/464,726.

Co-pending U.S. Appl. No. 12/578,262.

\* cited by examiner

MONOSILANE OR DISILANE DERIVATIVES AND METHOD FOR LOW TEMPERATURE DEPOSITION OF SILICON-CONTAINING FILMS USING THE SAME

CROSS-REFERENCE TO RELATED APPLICATION

This is a continuation, filed under the provisions of 35 USC §120, of U.S. patent application Ser. No. 10/683,501 filed Oct. 10, 2003, now U.S. Pat. No. 7,579,496 issued Aug. 25, 2009. The entire disclosure of said U.S. Pat. No. 7,579,496 is hereby incorporated herein by reference, for all purposes.

FIELD OF THE INVENTION

The present invention relates generally to the formation of silicon-containing films in the manufacture of semiconductor devices, and more specifically to compositions and methods for forming such films, e.g., films comprising silicon, silicon nitride ($Si_3N_4$), siliconoxynitride ($SiO_xN_y$), silicon dioxide ($SiO_2$), etc., low dielectric constant (k) thin silicon-containing films, high k gate silicate films and low temperature silicon epitaxial films.

DESCRIPTION OF THE RELATED ART

Silicon nitride ($Si_3N_4$) thin films are widely employed in the microelectronic industry as diffusion barriers, etch-stop layers, sidewall spacers, etc.

Deposition of silicon nitride films by chemical vapor deposition (CVD) techniques is a highly attractive methodology for forming such films. CVD precursors currently used include bis(tert-butylamino)silane (BTBAS) or silane/ammonia, but such precursors usually require deposition temperature higher than 600° C. for forming high quality $Si_3N_4$ films, which is incompatible with the next generation IC device manufacturing, where deposition temperature of below 500° C., and preferably about 450° C., is desired. Therefore, development of low-temperature silicon-containing CVD precursors is particularly desired.

Presently, hexachlorodisilane, $Cl_3Si$—$SiCl_3$, is being studied as a candidate precursor for low-temperature CVD formation of silicon nitride thin films upon reaction with ammonia gas. The drawbacks of using hexachlorodisilane in CVD processes include: (i) formation of large amount of $NH_4Cl$ during the process, which leads to the particle contamination and solid build-up in vacuum system and exhaust lines; (ii) possible chlorine incorporation in the chips, which could significantly reduce their life time and long-term performance; and (iii) the reaction by-products are known to be explosive. It is therefore desirable to develop new chlorine-free precursors that can be used for low-temperature CVD formation of silicon nitride thin films.

SUMMARY OF THE INVENTION

The present invention relates generally to the formation of silicon-containing films, such as films comprising silicon, silicon nitride ($Si_3N_4$), siliconoxynitride ($SiO_xN_y$), silicon dioxide ($SiO_2$), etc., silicon-containing low k films, high k gate silicates, and silicon epitaxial films, among which silicon nitride thin films are preferred, in the manufacture of semiconductor devices, and more specifically to compositions and methods for forming such silicon-containing films.

The present invention in one aspect relates to a group of halogen-free silane or disilane derivatives that are substituted with at least one alkylhydrazine functional groups and can be used as CVD precursors for deposition of silicon-containing thin films.

The silane derivatives of the present invention can be represented by the general formula of:

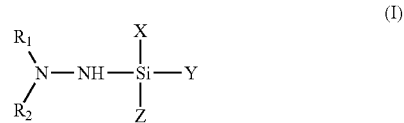

(I)

wherein $R_1$ and $R_2$ may be the same as or different from each another and are independently selected from the group consisting of H, $C_1$-$C_7$ alkyl, aryl, and $C_3$-$C_6$ cycloalkyl, or $R_1$ and $R_2$ together may form $C_3$-$C_6$ heterocyclic functional group with N, and wherein X, Y, and Z may be the same as or different from one another and are independently selected from the group consisting of H, $C_1$-$C_7$ alkyl, alkylamino, dialkylamino, and alkylhydrazido (e.g., $R_1R_2NNH$—, wherein $R_1$ and $R_2$ are same as described hereinabove).

Preferably, X, Y, and Z are all identical functional groups. More preferably, X, Y, and Z are all $C_1$-$C_7$ alkyl, such as methyl or ethyl. Alternatively but also preferably, X, Y, and Z are all alkylhydrazido (e.g., $R_1R_2NNH$—, wherein $R_1$ and $R_2$ are same as described hereinabove), such as N,N'-dimethylhydrazido or N,N'-diethylhydrazido.

The disilane derivatives of the present invention can be represented by the general formula of:

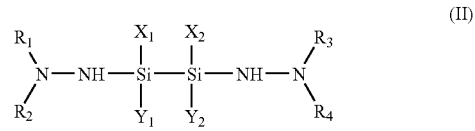

(II)

wherein $R_1$, $R_2$, $R_3$, and $R_4$ may be the same as or different from each another and are independently selected from the group consisting of H, $C_1$-$C_7$ alkyl, aryl, and $C_3$-$C_6$ cycloalkyl, or $R_1$ and $R_2$ together may form $C_3$-$C_6$ heterocyclic functional group with N, or $R_3$ and $R_4$ together may form $C_3$-$C_6$ heterocyclic functional group with N, and wherein $X_1$, $X_2$, $Y_1$, and $Y_2$ may be the same as or different from one another and are independently selected from the group consisting of H, $C_1$-$C_7$ alkyl, alkylamino, dialkylamino, and alkylhydrazido (e.g., $R_1R_2NNH$—, wherein $R_1$ and $R_2$ are same as described hereinabove).

Preferably, the disilane derivative compound of the present invention is characterized by functional groups that are symmetrically distributed in relation to the Si—Si bond.

Preferred silane or disilane derivative compounds of the present invention include, but are not limited to, $Me_3Si$ ($HNNMe_2$), $Si(HNNMe)_4$, $Me_2(HNNMe_2)Si$—$Si$ ($HNNMe_2)Me_2$, and $(HNBu^t)_2(HNNMe_2)Si$—$Si(HNNMe_2)$ $(HNBu^t)_2$, wherein Bu and Me are consistently used as the respective abbreviations of butyl and methyl throughout the text hereinafter.

Another aspect of the present invention relates to a method for forming a silicon-containing film on a substrate, comprising contacting a substrate under chemical vapor deposition conditions including a deposition temperature of below 550° C., preferably below 500° C., and more preferable below 450°

C., with a vapor of a silane or disilane derivative compound that is substituted with at least one alkylhydrazine functional group.

Still another aspect of the present invention relates to a method of making such silane or disilane derivative compounds, by reacting silane or disilane compounds comprising one or more halogen groups (i.e., halosilane or halodisilane) with alkylhydrazine in the presence of NEt$_3$, to substitute the one or more halogen groups of such silane or disilane compounds with alkylhydrazine functional groups.

A still further aspect of the present invention relates to a method of making Me$_3$Si(HNNMe$_2$), by reacting Me$_3$SiCl with approximately one molar ratio of H$_2$NNMe$_2$ in the presence of NEt$_3$, according to the following reaction:

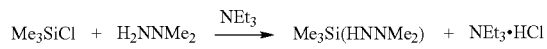

A still further aspect of the present invention relates to a method of making Si(HNNMe$_2$)$_4$, by reacting SiCl$_4$ with approximately four molar ratio of H$_2$NNMe$_2$ in the presence of NEt$_3$, according to the following reaction:

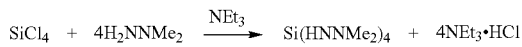

A still further aspect of the present invention relates to a method of making Me$_2$(HNNMe$_2$)Si—Si(HNNMe$_2$)Me$_2$, by reacting Me$_2$(Cl)Si—Si(Cl)Me$_2$ with approximately two molar ratio of H$_2$NNMe$_2$ in the presence of NEt$_3$, according to the following reaction:

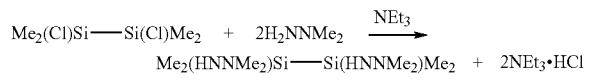

A still further aspect of the present invention relates to a method of making, by reacting (HNBu$^t$)$_2$(HNNMe$_2$)Si—Si(HNNMe$_2$)(HNBu$^t$)$_2$, by reacting (HNBu$^t$)$_2$(Cl)Si—Si(Cl)(HNBu$^t$)$_2$ with approximately two molar ratio of LiHNNMe$_2$, according to the following reaction:

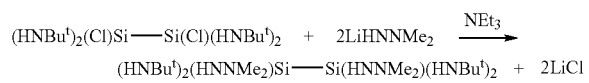

Other aspects, features and embodiments of the invention will be more fully apparent from the ensuing disclosure and appended claims.

DETAILED DESCRIPTION OF THE INVENTION AND PREFERRED EMBODIMENTS THEREOF

Figure 1:
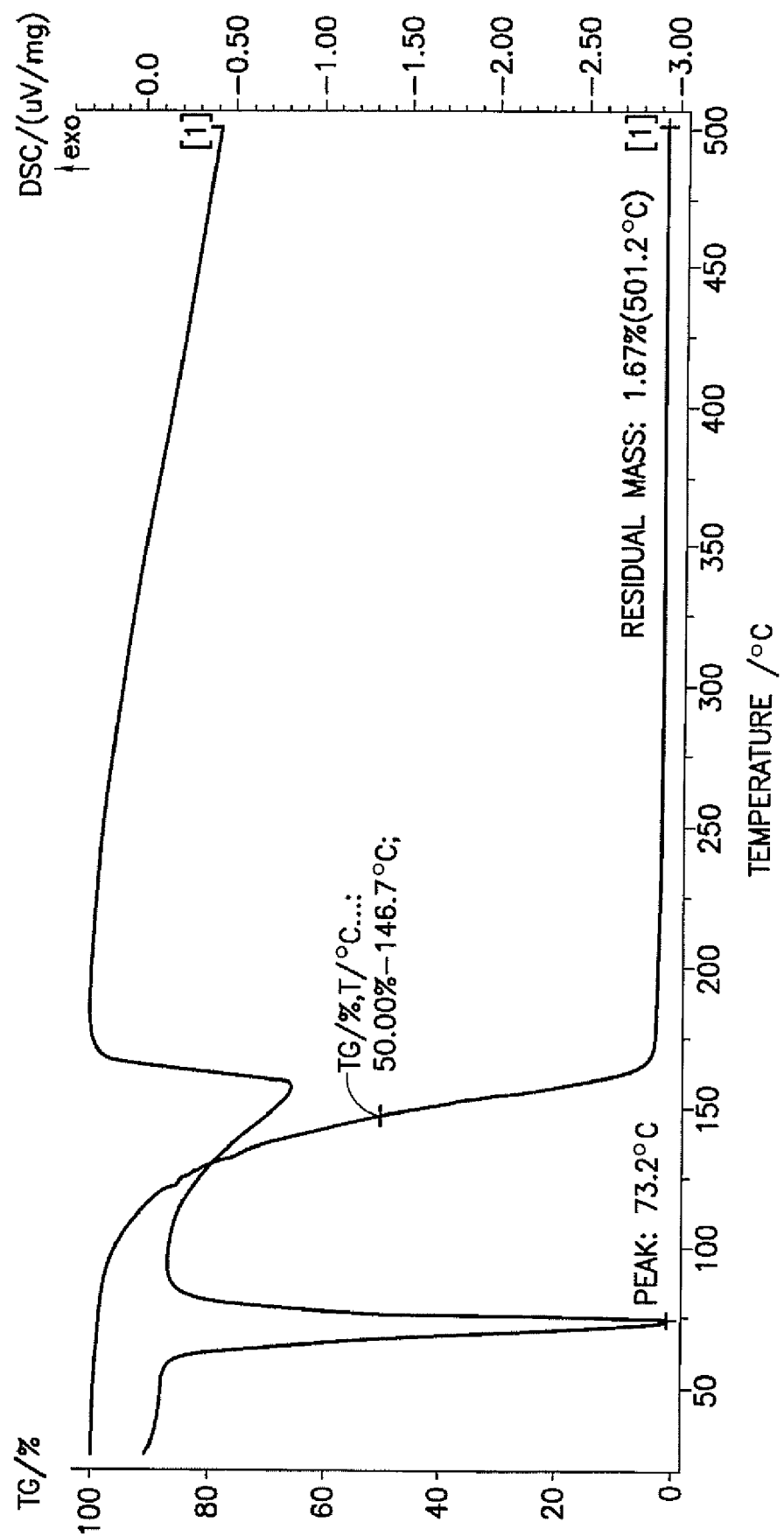
FIG. 1 is a STA plot for Si(HNNMe$_2$)$_4$.

The present invention relates to silicon precursors for CVD formation of films on substrates, such as silicon precursors for forming low k dielectric films, high k gate silicates, low temperature silicon epitaxial films, and films comprising silicon, silicon oxide, silicon oxynitride, silicon nitride, etc., as well as to corresponding processes for forming such films with such precursors.

Silane or disilane derivatives that contain one or more alkylhydrazine functional groups, free of any halogen substitutes, are found particularly suitable for low-temperature deposition of silicon nitride thin films, since the bond-strength of the nitrogen-nitrogen single bond in the hydrazine functional group relatively weak. Moreover, use of such halogen-free silicon precursors avoids the various problems involved in previous CVD processes using hexachlorodisilane.

Preferred silane derivatives of the present invention can be represented by the general formula of:

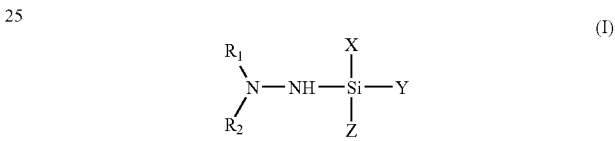

wherein R$_1$ and R$_2$ may be the same as or different from each another and are independently selected from the group consisting of H, C$_1$-C$_7$ alkyl, aryl, and C$_3$-C$_6$ cycloalkyl, or R$_1$ and R$_2$ together may form C$_3$-C$_6$ heterocyclic functional group with N, and wherein X, Y, and Z may be the same as or different from one another and are independently selected from the group consisting of H, C$_1$-C$_7$ alkyl, alkylamino, dialkylamino, and alkylhydrazido (e.g., R$_1$R$_2$NNH—, wherein R$_1$ and R$_2$ are same as described hereinabove).

Preferred disilane derivatives of the present invention can be represented by the general formula of:

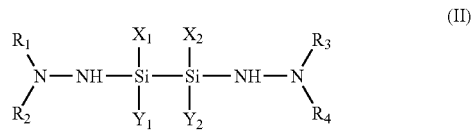

wherein R$_1$, R$_2$, R$_3$, and R$_4$ may be the same as or different from each another and are independently selected from the group consisting of H, C$_1$-C$_7$ alkyl, aryl, and C$_3$-C$_6$ cycloalkyl, or R$_1$ and R$_2$ together may form C$_3$-C$_6$ heterocyclic functional group with N$_1$ or R$_3$ and R$_4$ together may form C$_3$-C$_6$ heterocyclic functional group with N, and wherein X$_1$, X$_2$, Y$_1$, and Y$_2$ may be the same as or different from one another and are independently selected from the group consisting of H, C$_1$-C$_7$ alkyl, alkylamino, dialkylamino, and alkylhydrazido (e.g., R$_1$R$_2$NNH—, wherein R$_1$ and R$_2$ are same as described hereinabove).

Disilane derivative compounds that are substantially symmetrical in structure in relation to the Si—Si bond, i.e., all functional groups of such compounds being symmetrically distributed in relation to the Si—Si bond, are particularly preferred for practicing of the present invention. For example, such disilane derivative compounds may contain two identical alkylhydrazine functional groups and four identical $C_1$-$C_5$ alkyl functional groups that are symmetrically distributed in relation to the Si—Si bond, such as $Me_2$(HNNMe)Si—Si(HNNMe)$Me_2$.

The silane or disilane derivative compounds as described hereinabove are advantageously characterized by a vaporization temperature of less than 300° C. Moreover, such compounds can be transported in vapor form at less than 300° C. and under atmospheric pressure, with no or little (<2%) residual material. The silicon-containing films that can be formed using such disilane precursor compounds include $Si_3N_4$ thin films, high k gate silicates and silicon epitaxial films. In a particularly preferred embodiment of the invention, the films formed using such silane or disilane precursors comprise silicon nitride.

Preferred silane or disilane compounds of the above-described formulas include, but are not limited to, $Me_3Si(HNNMe_2)$, $Si(HNNMe_2)_4$, $Me_2(HNNMe_2)Si$—$Si(HNNMe_2)Me_2$, and $(HNBu^r)_2(HNNMe_2)Si$—$Si(HNNMe_2)(HNBu^r)_2$.

Synthesis and characterization of the above-listed preferred compounds is described in the following examples:

Example 1

Synthesis and Characterization of $Me_3Si(HNNMe_2)$

A 3 L flask was filled with a solution comprising 2.5 L hexanes, 54.0 grams (0.53 mol) $NEt_3$, and 30 grams (0.50 mol) of $H_2NNMe_2$. 58 grams (0.53 mol) $Me_3SiCl$, as dissolved in 500 mL of hexanes, was slowly added into the 3 L flask at 0° C. White precipitate was observed during the addition of $Me_3SiCl$. After the completion of the reaction, the mixture was warmed to room temperature, stirred overnight, and then filtered. The crude yield was in 80%. Regular distillation procedure was used to purify the end product, which has a boiling point of approximately 100° C. $^1H$ NMR($C_6D_6$): δ 0.15 (s, 9H, —$SiCH_3$), 1.73 (br, 1H, —NH), 2.22 (s, 6H, —$NCH_3$). $^{13}C\{^1H\}$ NMR($C_6D_6$): δ −0.54 (—$SiCH_3$), 52.4 (—$NCH_3$). Mass spectrum: m/z 132 [$M^+$], 117 [$M^+$−Me)], 102 [$M^+$−2Me)], 88 [$M^+$−3Me)], 73 [$M^+$−(—$HNNMe_2$)].

$Me_3Si(HNNMe_2)$ is a liquid at room temperature.

Example 2

Synthesis and Characterization of $Si(HNNMe_2)_4$

A 250 mL flask was filled with a solution comprising 200 mL hexanes, 12.2 grams (120.7 mmol) $NEt_3$, and 7.25 grams (120.7 mmol) $HNNMe_2$. 5.0 grams (29.4 mmol) $SiCl_4$, as dissolved in 15 mL of hexanes, was slowly added into the 250 mL flask at 0° C. White precipitate was observed during the addition of $SiCl_4$. After the completion of the reaction, the mixture was stirred overnight and then filtered at room temperature. All volatile materials were removed from the filtrate under vacuum. The crude yield was in 65% (5.0 g, 19.0 mmol). Purified end product was obtained by recrystallization in hexanes at −5° C. $^1H$ NMR($C_6D_6$): δ 2.42 (s, 24H, —$CH_3$), 2.47 (br, 4H, —HN). $^{13}C\{^1H\}$ NMR($C_6D_6$): δ 52.7 (—$CH_3$). $C_8H_{28}N_8Si$. Found (calculated) C, 36.15% (36.34%), H, 11.02% (10.67%), N, 42.66% (42.37%).

$Si(HNNMe_2)_4$ is a solid material having a melting temperature of approximately 73° C. The thermal stability of $Si(HNNMe_2)_4$ in solution at 100° C. was monitored by proton NMR study for 7 days, and no significant decomposition was detected.

FIG. 1 is a STA plot for $Si(HNNMe_2)_4$, indicating that $Si(HNNMe_2)_4$ can be transported completely with very little (<2%) residual material at 500° C.

Figure 2:
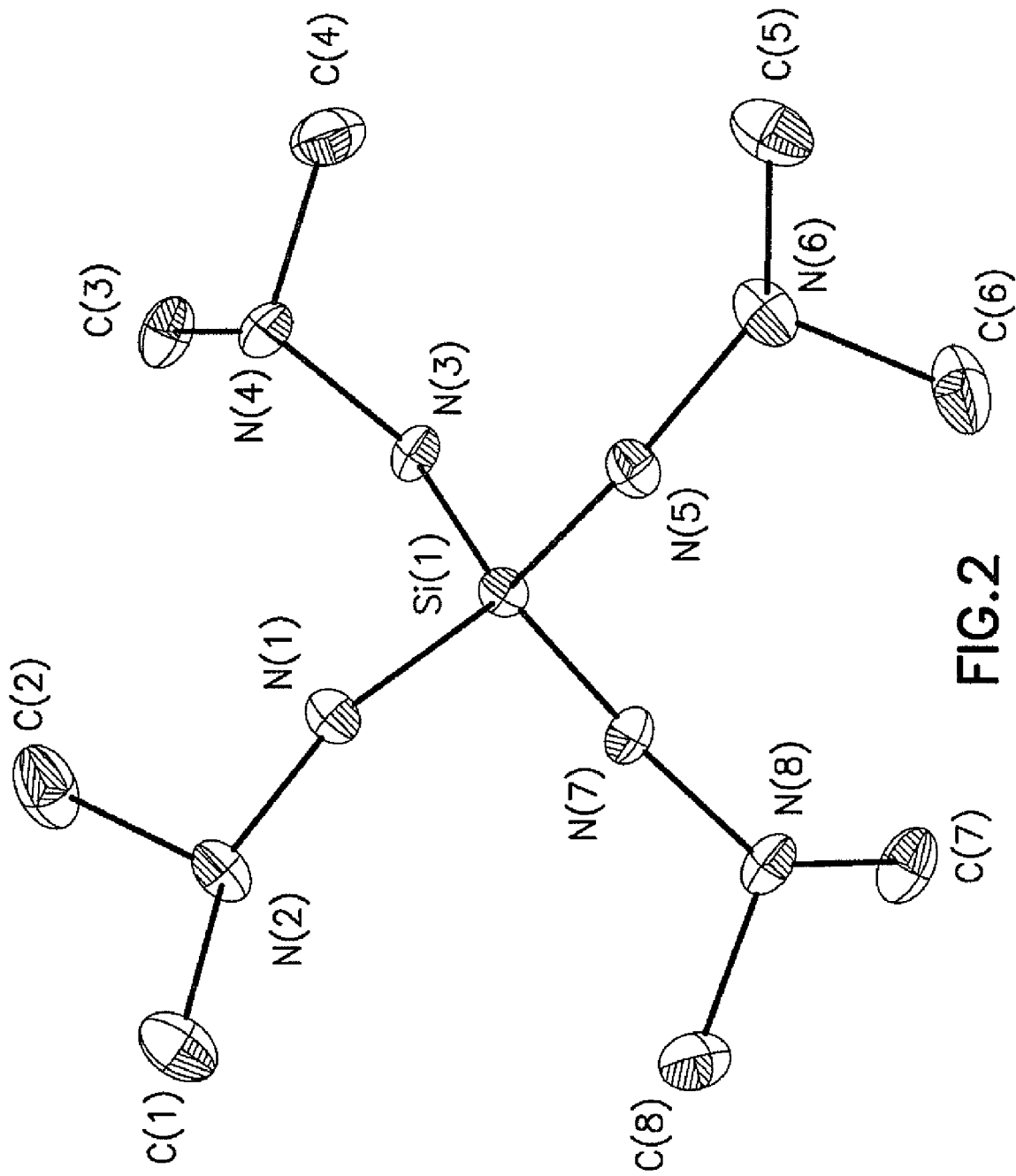
FIG. 2 is an X-ray crystal structure of the compound Si(HNNMe$_2$)$_4$.

FIG. 2 shows the X-ray crystal structure of $Si(HNNMe_2)_4$.

Example 3

Synthesis and Characterization of $Me_2(HNNMe_2)$Si—$Si(HNNMe_2)M_2$

A 3 L flask was filled with a solution comprising 2.5 L hexanes, 57 grams (561 mmol) anhydrous $NEt_3$, and 50 grams (267 mmol) of $Me_2$(Cl)Si—Si(Cl)$Me_2$. 34 grams (561 mmol) $H_2NNMe_2$, as dissolved in 100 mL of diethyl ether, was slowly added into the 3 L flask at room temperature. White precipitate was observed during the addition of $H_2NNMe_2$. After the completion of the addition of $H_2NNMe_2$, the mixture was stirred overnight, and then filtered. All volatile materials were removed from the filtrate under vacuum. The crude yield was in 86% (54 g, 230 mmol). Vacuum distillation procedure was used to purify the end product, which has a boiling point of approximately 45° C. at 35 mTorr. $^1H$ NMR($C_6D_6$): δ 0.33 (s, 12H, —$CH_3Si$), 1.90 (br, 2H, —HN), 2.27 (s, 12H, —$CH_3N$). $^{13}C\{^1H\}$ NMR ($C_6D_6$): δ −0.68 (—$SiCH_3$), 52.6 (—$NCH_3$). Mass spectrum: m/z 175 [$M^+$−(—$HNNMe_2$)], 132 [$M^+$−(—$HNNMe_2$)−(—$NMe_2$)], 116 [$M^+$−(—$SiMe_2(HNNMe_2)$)]. $C_8H_{26}N_4Si_2$. Found (calculated) C, 40.81% (40.98%), H, 10.99% (11.18%), and N, 23.67% (23.89%).

Figure 3:
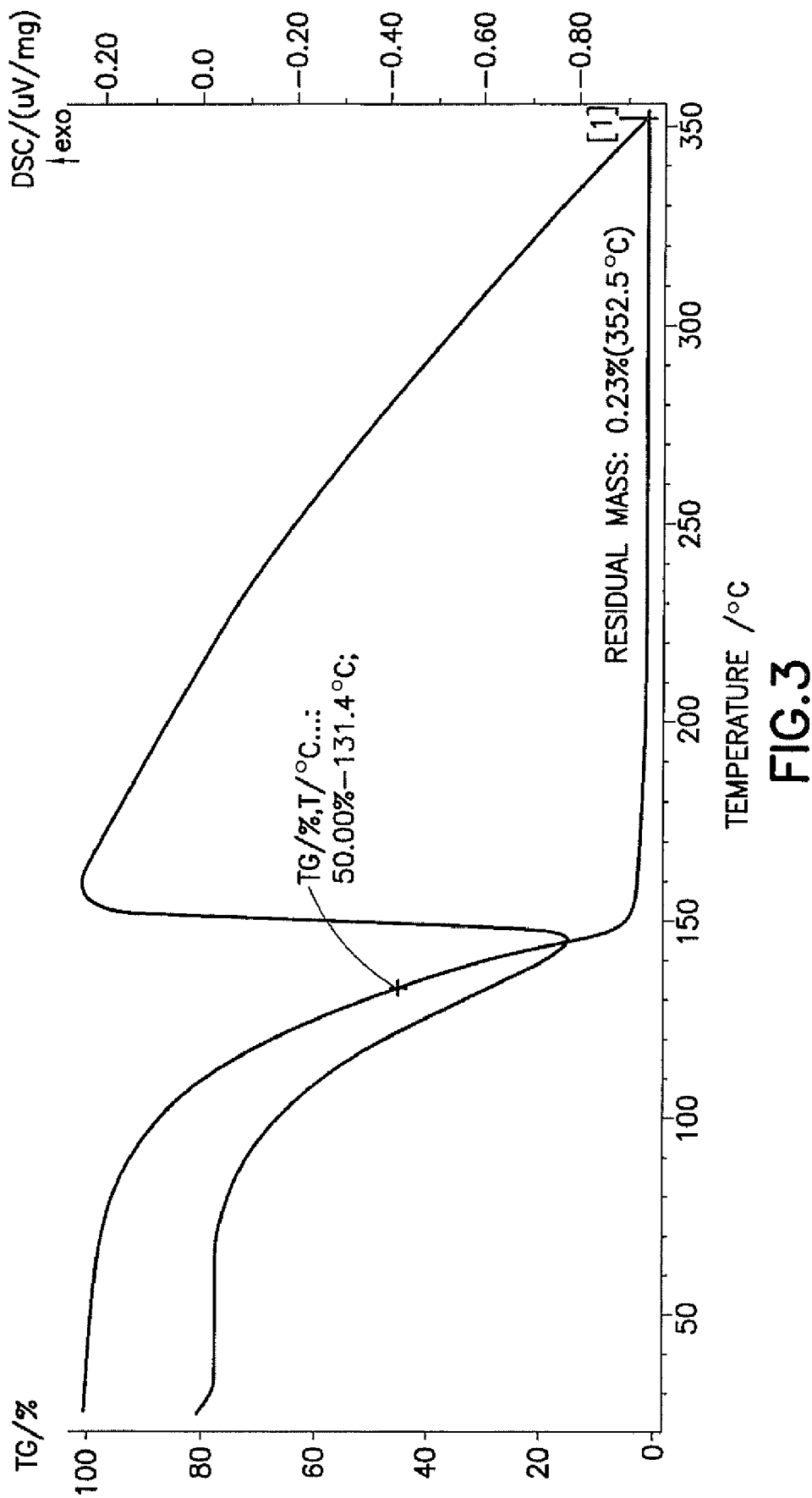
FIG. 3 is a STA plot for Me$_2$(HNNMe$_2$)Si—Si(HNNMe$_2$)Me$_2$.

FIG. 3 shows the STA plot for $Me_4Si_2(HNNMe_2)_2$, which is a liquid at room temperature and can be transported in its vapor form completely with very little (<1%) residual material at about 350° C. The thermal stability of $Me_4Si_2(HNNMe_2)_2$ in solution at 100° C. was monitored by proton NMR study for 7 days, and no significant decomposition was detected.

Example 4

Synthesis and Characterization of $(HNBu^r)_2(HNNMe_2)Si$—$Si(HNNMe_2)(HNBu^r)_2$ A 250 mL flask filled with a solution comprising 120 mL of hexanes and 15.8 mL (1.6M, 25.3 mmol) of methyllithium ether solution. 1.52 grams (25.3 mmol) of $H_2NNMe$ was slowly bubbled into the 250 mL flask at 0° C. Upon completion of the addition, the reaction flask was allowed to warm to room temperature and stirred for an additional hour. To this flask, a 50 mL of diethyl ether solution containing 5 grams (12 mmol) of $(HNBu^r)_2$(Cl)Si—Si(Cl)$(HNBu^r)_2$ was slowly added at 0° C. The mixture was stirred overnight, and then refluxed for an additional four hours. After it was cooled to room temperature, it was filtered. All volatile materials were removed from the filtrate under vacuum. The crude yield was in 72% (4.0 grams, 8.64 mmol). Purified end product was obtained by recrystallization in hexanes at −20° C. $^1H$ NMR ($C_6D_6$): δ 1.40 (s, 36H, —C($CH_3$)$_3$), 1.55 (br, 4H, —H$\underline{H}$C($CH_3$)$_3$), 2.13 (br, 2H, —N$\underline{H}$N($CH_3$)$_2$), 2.43 (s, 12H, —NHN(C$\underline{H}_3$)$_2$). $^{13}C\{^1H\}$ NMR ($C_6D_6$): δ 34.3 (—NHC($\underline{C}H_3$)$_3$), 49.5 (—NH$\underline{C}$($CH_3$)$_3$), 52.6 (—NHN($\underline{C}H_3$)$_2$). $C_{20}H_{54}N_8Si_2$. Found (calculated) C, 51.76% (51.90%), H, 11.76% (11.76%), N, 24.28% (24.21%).

Figure 4:
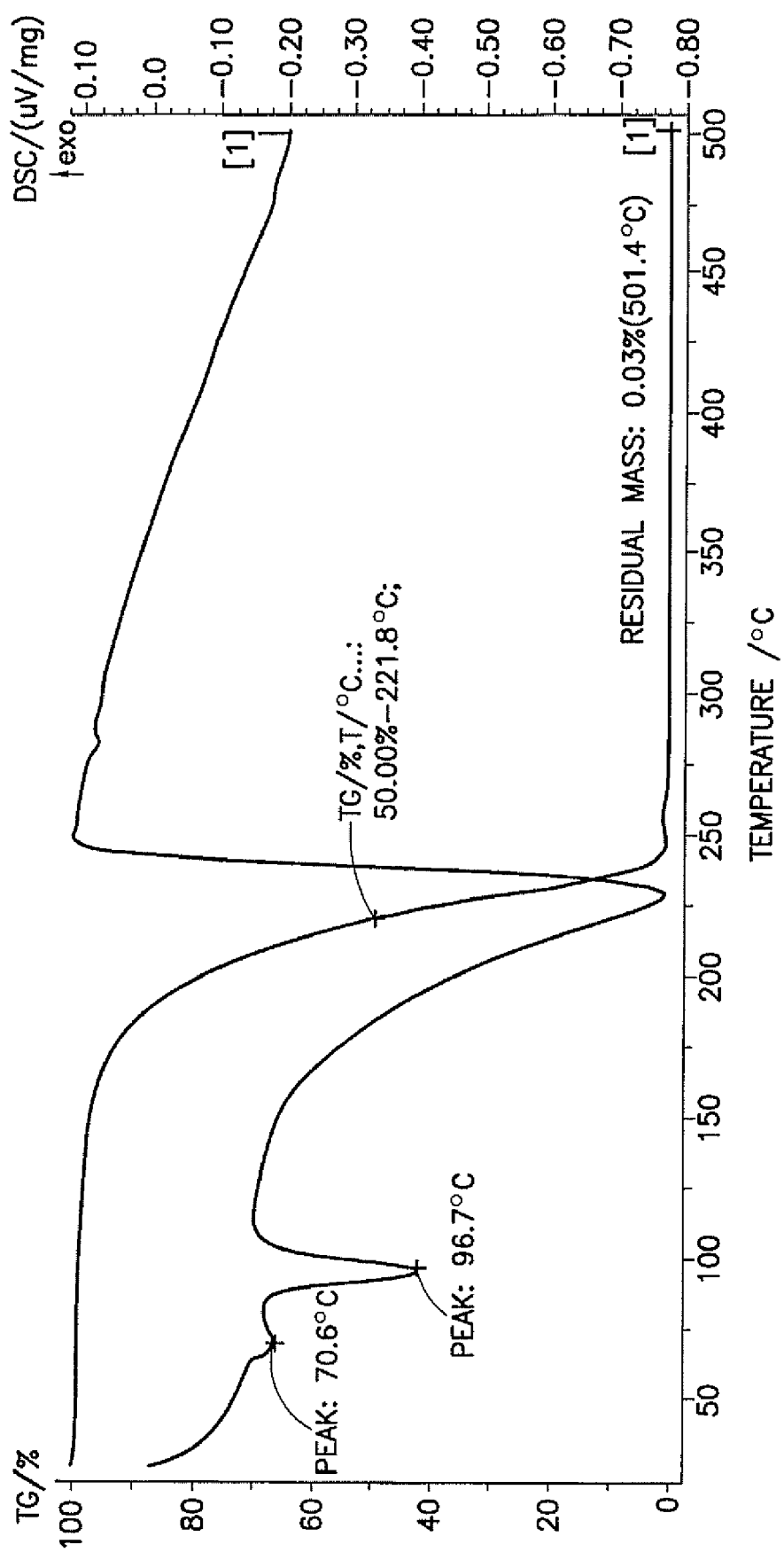
FIG. 4 is a STA plot for (HNBu$^t$)$_2$(HNNMe$_2$)Si—Si(HNNMe$_2$)(HNBu$^t$)$_2$.

FIG. 4 shows the STA plot for $(HNBu^r)_2(HNNMe_2)Si$—$Si(HNNMe_2)(HNBu^r)_2$, which is a solid at room temperature and can be transported completely with very little (~0.03%) residual material at about 500° C.

Such silane or disilane derivative compounds as described hereinabove can be used for low-pressure CVD deposition of various silicon-containing films, including silicon nitride thin films, consistent with the disclosure in U.S. patent application Ser. No. 10/294,431 for "Composition and Method for Low Temperature Deposition of Silicon-Containing Films Including Silicon Nitride, Silicon Dioxide and/or Silicon-Oxynitride" filed on Nov. 14, 2002, now U.S. Pat. No. 7,531,679 issued May 12, 2009, the content of which is incorporated by reference in its entirety for all purposes.

While the invention has been described herein with reference to various specific embodiments, it will be appreciated that the invention is not thus limited, and extends to and encompasses various other modifications and embodiments, as will be appreciated by those ordinarily skilled in the art. Accordingly, the invention is intended to be broadly construed and interpreted, in accordance with the ensuing claims.

What is claimed is:

1. A method of forming a silicon-containing film on a substrate, comprising contacting a substrate under vapor deposition conditions comprising a temperature below 450° C. with a vapor of a disilane compound of the formula:

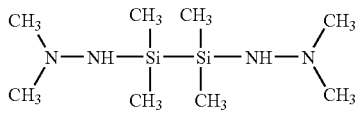

to form said silicon-containing film on the substrate.

2. The method of claim 1, wherein said film comprises silicon dioxide.

3. The method of claim 1, wherein said film comprises silicon nitride.

4. The method of claim 1, wherein said film comprises siliconoxynitride.

5. The method of claim 1, wherein said film comprises a low dielectric constant silicon-containing film.

6. The method of claim 1, wherein said film comprises a gate silicate film.

7. The method of claim 1, wherein said film comprises an epitaxial silicon-containing film.

8. The method of claim 1, wherein the substrate comprises a semiconductor device substrate.

9. The method of claim 1, wherein said vapor deposition comprises chemical vapor deposition.

10. The method of claim 1, conducted in an ULSI device fabrication process.

11. The method of claim 1, wherein said vapor is transported to said contacting at temperature below 300° C.

12. The method of claim 11, wherein said vapor is transported at atmospheric pressure.

13. A method of manufacturing a semiconductor device, comprising using a silicon precursor of the formula:

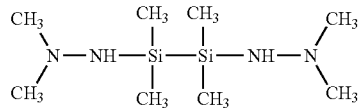

to deposit at temperature below 450° C. a silicon-containing film on a substrate for said semiconductor device.

14. The method of claim 13, wherein the silicon precursor is used to form a silicon nitride material in said semiconductor device.

15. The method of claim 14, wherein said silicon precursor is used to form a semiconductor device diffusion barrier layer.

16. The method of claim 14, wherein said silicon precursor is used to form a semiconductor device etch-stop layer.

* * * * *

UNITED STATES PATENT AND TRADEMARK OFFICE
CERTIFICATE OF CORRECTION

PATENT NO. : 7,863,203 B2  Page 1 of 1
APPLICATION NO. : 12/019557
DATED : January 4, 2011
INVENTOR(S) : Ziyun Wang It is certified that error appears in the above-identified patent and that said Letters Patent is hereby corrected as shown below:

Title Page, Item (74) Attorney, Agent, or Firm: "Margaret Chappi" should be -- Margaret Chappuis --.

Signed and Sealed this
Third Day of May, 2011

David J. Kappos
*Director of the United States Patent and Trademark Office*